United States Patent
Akimoto et al.

(10) Patent No.: US 6,432,468 B1
(45) Date of Patent: Aug. 13, 2002

(54) DOMESTIC FOWL EGGS HAVING A HIGH CONTENT OF HIGHLY UNSATURATED FATTY ACID, THEIR PRODUCTION PROCESS AND THEIR USE

(75) Inventors: Kengo Akimoto; Kenichi Higashiyama, both of Osaka; Takafumi Ishihara; Teruyuki Kanada, both of Okayama; Yoshiharu Tanaka, Kawagoe; Motoharu Arai, Tokyo, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 08/776,297
(22) PCT Filed: May 29, 1996
(86) PCT No.: PCT/JP96/01453
§ 371 (c)(1),
(2), (4) Date: Jan. 30, 1997
(87) PCT Pub. No.: WO96/38051
PCT Pub. Date: Dec. 5, 1996

(30) Foreign Application Priority Data

| May 30, 1995 | (JP) | 7-131510 |
| Jun. 2, 1995 | (JP) | 7-136697 |
| Sep. 21, 1995 | (JP) | 7-243285 |
| Sep. 22, 1995 | (JP) | 7-244630 |

(51) Int. Cl.[7] .................... A23L 1/32; A23D 7/00; A23K 1/16; A23K 1/18
(52) U.S. Cl. .................. 426/614; 426/601; 426/608; 426/2; 554/8; 435/134; 435/243
(58) Field of Search .................. 426/614, 601, 426/608, 2, 49; 435/134, 243; 554/8

(56) References Cited

U.S. PATENT DOCUMENTS

| 4,738,853 A | 4/1988 | Horrobin |
| 4,868,001 A | 9/1989 | Maruta |
| 4,918,104 A | 4/1990 | Weiss et al. |
| 5,466,842 A | 11/1995 | Heidlas et al. |
| 5,583,019 A | * 12/1996 | Barclay ........... 435/134 |
| 5,589,357 A | * 12/1996 | Martinez et al. ........... 435/68.1 |

FOREIGN PATENT DOCUMENTS

| EP | 0 157 619 A2 | 10/1985 |
| EP | 0 611 528 A1 | 8/1994 |
| EP | 0 616 025 A1 | 9/1994 |
| JP | 60-105471 | 6/1985 |
| JP | 61035763 | 2/1986 |
| JP | 62-120340 | 6/1987 |
| JP | 63-98355 | 4/1988 |
| JP | 1-215245 | 8/1989 |
| JP | 3-27184 | 4/1991 |
| JP | 3-36493 | 5/1991 |
| JP | 4-360653 | 12/1992 |
| JP | 5-51271 | 8/1993 |
| JP | 6-237703 | 8/1994 |
| JP | 07227221 | 8/1995 |
| JP | 8-80164 | 3/1996 |
| KR | 95-9532 | 8/1995 |
| WO | 96/00016 | 1/1996 |

OTHER PUBLICATIONS

Database Abstract. AN 95(01):Q0001 FSTA. taken from Journal of Japanese Society of Nutrition and Food Science. (1994) 47 (1) pp. 23–27. Author: Suzuki et al.*
Chemical Abstracts 117:209239p, vol. 117, (1992), p. 209232.
JP 59039258 A (abstract), Nisshin Flour Mining Co., Mar. 3, 1984.
JP 05–292853 A (abstract) Kobayashii, Nov. 9, 1993, World Patents Index, Derwent Publications, Ltd.
Mitsuhiro Furuse et al., "Effect of Gama–Linolenic Acid on Lipid Metabolishm in Laying Hens", 1992, Comp. Biochem. Physiol., vol. 101A, No. 1, pp. 167–169.

* cited by examiner

Primary Examiner—Anthony J. Weier
(74) Attorney, Agent, or Firm—Burns, Doane, Swecker & Mathis, L.L.P.

(57) ABSTRACT

The present invention provides domestic fowl eggs having a high content of arachidonic acid and optionally docosahexaenoic acid obtained by feeding egg-laying domestic fowls ω6 highly unsaturated fatty acids and optionally ω3 highly unsaturated fatty acids, their production process, a lipid that originates from them, and a food that contains said lipid.

38 Claims, No Drawings

DOMESTIC FOWL EGGS HAVING A HIGH CONTENT OF HIGHLY UNSATURATED FATTY ACID, THEIR PRODUCTION PROCESS AND THEIR USE

TECHNICAL FIELD

The present invention relates to domestic fowl eggs having a high content of arachidonic acid and optionally docosahexaenoic acid, and a process for production thereof from egg-laying domestic fowls raised by feeding ω6 highly unsaturated fatty acid and optionally ω3 highly unsaturated fatty acid, as well as lipid having a high content of arachidonic acid and optionally docosahexaenoic acid, obtained from said domestic fowl eggs, a process for production thereof, and their use.

BACKGROUND ART

Although eggs having a high degree of nutritional value and are excellent foods that contain a good balance of nutrients, due to their high cholesterol content, their consumption must be restricted. In recent years, research has therefore been conducted to introduce various drugs into eggs to inhibit increases in blood cholesterol levels, and numerous research has been reported.

On the other hand, after it was reported that ω3 highly unsaturated fatty acids contained in fish oil have an effect of lowering blood cholesterol (Japanese Unexamined Patent Publication No. 54-154533), a technology was developed in which large amounts of docosahexaenoic acid and eicosapentaenoic acid are introduced into the egg yolks of domestic fowl eggs by raising egg-laying domestic fowls on feed to which was added fish oil containing ω3 highly unsaturated fatty acids (Japanese Examined Patent Publication No. 3-36493).

However, reports of substances having the effect of lowering blood cholesterol were not limited to ω3 highly unsaturated fatty acid. This effect is also observed in ω6 highly unsaturated fatty acids such as γ-linolenic acid (Agric. Biol. Chem., 50, 2483–2491 (1986)), dihomo-γ-linolenic acid and arachidonic acid ("Lipid Metabolism of Liver Disease", Chugai Medical Co., Ltd., 1994, pp. 127–130). However, a method of for increasing amounts of ω6 highly unsaturated fatty acids, and particularly arachidonic acid, in eggs has not yet been developed. Moreover, in recent years, questions have been raised regarding the ratio of ω6 highly unsaturated fatty acids and ω3 highly unsaturated fatty acids. Consequently, instead of the conventional technology for increasing amount of eicosapentaenoic acid or docosahexaenoic acid in egg yolks, there has been a strong desire for a method of containing ω6 highly unsaturated fatty acid and ω3 highly unsaturated fatty acid in egg yolks in a favorable balance.

In view of these circumstances, it is stated for the amounts of ingested fatty acids in the section concerning ingestion of fatty acids in the Nutritional Requirements of the Japanese (5th Revision) that, "Consistent opinions have not yet been obtained regarding the ratio of ingestion of n-6 (ω6) fatty acids and n-3 (ω3) fatty acids. The results of a nutritional survey of Japanese showed that many of those surveyed fatty acids are ingested in the ratio of roughly 4:1, and this ratio is considered to be suitable at the present stage." (Ministry of Health and Welfare, Health Service Bureau, Health Promotion and Nutrition Dept. ed.: "Nutritional Requirements of the Japanese, 5th Revision", 1st edition, 1994, pp. 56–58).

In addition, it has also been recently reported that arachidonic acid and docosahexaenoic acid are contained in mother's milk, and that they are useful in the growth and development of infants ("Advances in Polyunsaturated Fatty Acid Research", Elsevier Science Publishers, 1993, pp 261–264). Moreover, their importance has also been reported in the height and brain development of the fetus (Proc. Natl. Acad. Sci. USA, 90, 1073–1077 (1993), Lancet, 344, 1319–1322 (1994)).

With this in mind, attempts were made to add arachidonic acid and docosahexaenoic acid, for which there are large differences in the fatty acid composition between mother's milk and infant formula, to infant formula. Although infant formula containing fish oil is currently available on the market for the purpose of adding docosahexaenoic acid to a infant formula, eicosapentaenoic acid contained in fish oil is inherently hardly contained at all in mother's milk. According to the results of recent research, this substance is not always favorable for the growth and development of premature infants ("Advances in Polyunsaturated Fatty Acid Research", Elsevier Science Publishers, 1993, pp. 261–264). U.S. Pat. No. 5,374,657 describes an invention relating to an oil to be added to milk product for infants, which oil blend comprises an edible oil in microbial cells containing docosahexaenoic acid and an edible oil in microbial cells containing arachidonic acid, but a small amount of eicosapentaenoic acid. However, since this involves direct administration of microbiological oil to premature infants and nursing infants, considerable cautions are required in terms of safety.

On the other hand, U.S. Pat. No. 4,670,285 discloses an amount of fatty acids such as arachidonic acid required by infants, and a blend of egg yolk oil and vegetable oil as an edible fat product for incorporation into an infant formula for providing these fatty acids. The egg yolk lipid used here can be said to have a lower amount of eicosapentaenoic acid and be an extremely safe raw material in comparison with the above-mentioned fish oil and microbial oil. However, since this egg yolk lipid contains only small amounts of arachidonic acid and docosahexaenoic acid (roughly 1.5% arachidonic acid and roughly 1.7% docosahexaenoic acid per the total fatty acids in the egg yolk lipid), it is uneconomical.

ω3 highly unsaturated fatty acids have an abundant supply source, namely fish oil which have no problems whatsoever in terms of safety. However, there are surprisingly few supply sources of ω6 highly unsaturated fatty acids, such as arachidonic acid. For example, although it is known that large amount of arachidonic acid are contained in liver, there are few opportunities for its consumption as a food. In addition, it is present only in small amounts in other meats (roasts or filet portions).

Therefore, extensive efforts were made to seek a supply source of ω6 highly unsaturated fatty acids such as arachidonic acid in the microbial world. A technology was developed relating to the production of ω6 highly unsaturated fatty acids by microorganisms represented by molds belonging to genus Mortierella, subgenus Mortierella (Japanese Unexamined Patent Publication No. 63-044891). However, although this technology was considered to have a high degree of safety, it did not expand significantly due to the problem of being of microbial origin.

Thus, there was a strong desire for the development of domestic fowl eggs fortified with arachidonic acid and optionally docosahexaenoic acid, as well as a lipid having a high content of arachidonic acid, and optionally docosahexaenoic acid extracted from those domestic fowl eggs for use as safe sources of arachidonic acid.

DISCLOSURE OF THE INVENTION

Thus, the present invention provides domestic fowl eggs having a high content of arachidonic acid and optionally docosahexaenoic acid, and a process for production thereof, as well as a lipid having a high content of arachidonic acid and optionally docosahexaenoic acid obtained from said domestic fowl eggs, a process for production thereof and its use.

As a result of various research to achieve the above-mentioned object, the inventors of the present invention found that domestic fowl eggs obtained by feeding egg-laying domestic fowls with ω6 highly unsaturated fatty acids and optionally ω3 highly unsaturated fatty acids have a high contents of arachidonic acid and optionally docosahexaenoic acid, that are at least 2%, respectively, of the total amount of fatty acids in the egg yolk, thereby leading to completion of the present invention.

Thus, the present invention provides domestic fowl eggs having a high content of arachidonic acid and optionally docosahexaenoic acid obtained by feeding egg-laying domestic fowls with ω6 highly unsaturated fatty acid and optionally ω3 highly unsaturated fatty acid.

Moreover, the present invention provides a production process of domestic fowl eggs having a high content of arachidonic acid and optionally docosahexaenoic acid comprising feeding egg-laying domestic fowls with ω6 highly unsaturated fatty acid and optionally ω3 highly unsaturated fatty acid.

In addition, the present invention provides a lipid having a high content of arachidonic acid and optionally docosahexaenoic acid obtained from domestic fowl eggs obtained by feeding egg-laying domestic fowls with ω6 highly unsaturated fatty acid and optionally ω3 highly unsaturated fatty acid.

Moreover, the present invention provides a production process of a lipid having a high content of arachidonic acid and optionally docosahexaenoic acid comprising extracting lipid having a high content of arachidonic acid and optionally docosahexaenoic acid from domestic fowl eggs obtained by feeding egg-laying domestic fowls with ω6 highly unsaturated fatty acid and optionally ω3 highly unsaturated fatty acid.

Moreover, the present invention provides a food having arachidonic acid and optionally docosahexaenoic acid, containing at least 0.001% by weight of a lipid having a high content of arachidonic acid and optionally docosahexaenoic acid obtained by extracting from domestic fowl eggs obtained by feeding egg-laying domestic fowls with ω6 highly unsaturated fatty acid and optionally ω3 highly unsaturated fatty acid.

In a preferable embodiment of the above-mentioned invention, the ω6 highly unsaturated fatty acid is at least one of the fatty acids selected from the group consisting of γ-linolenic acid, dihomo-γ-linolenic acid and arachidonic acid. This is preferably used in at least one of the forms selected from the group consisting of free fatty acid, salt, ester, triacylglycerol, diacylglycerol, monoacylglycerol, glycerophospholipid, glyceroglycolipid, sphingophospholipid and sphingoglycolipid.

Preferably, ω6 highly unsaturated fatty acid is given to domestic fowls either alone or as a mixture in the form of an oil or extract residue obtained by extracting from dried or wet microbial cells of a microorganism having the ability to produce arachidonic acid, or dried or wet microbial cells of a microorganism having the ability to produce arachidonic acid.

Microorganisms having the ability to produce arachidonic acid are preferably of the genus Mortierella, Conidiobolus, Pythium, Phytophthora, Penicillium, Cladosporium, Mucor, Fusarium, Aspergillus, Rhodotorula, Entomophthora, Echinosporangium and Saprolegnia.

Preferably, ω3 highly unsaturated fatty acid is at least one of the fatty acids selected from the group consisting of α-linolenic acid, 8,11,14,17-eicosatetraenoic acid, 5,8,11,14,17-eicosapentaenoic acid, 7,10,13,16,19-docosapentaenoic acid and 4,7,10,13,16,19-docosahexaenoic acid. These are preferably used in at least one of the forms selected from the group consisting of free fatty acid, salt, ester, triacylglycerol, diacylglycerol, monoacylglycerol, glyerophospholipid, glyceroglycolipid, sphingophospholipid and sphingoglycolipid.

Preferably, ω3 highly unsaturated fatty acid is given to domestic fowls either alone or as a mixture in the form of fish oil, fish powder, fish refuse, fish oil extract, an oil or extract residue obtained by extracting from dried or wet microbial cells of a microorganism having the ability to produce docosahexaenoic acid, or dried or wet microbial cells of a microorganism having the ability to produce docosahexaenoic acid.

Microorganisms having the ability to produce docosahexaenoic acid are preferably of the genus Crypthecodimium, Isochrysis, Nanochloropsis, Chaetoceros, Phaeodactylum, Amphidinium, Gonyaulax, Peridimium, Chroomonas, Cryptomonas, Hemiselmis, Chilomonas, Chlorella, Histiobranchus, Coryphaenoides, Thraustchytrium, Schizochytrium Conidiobolus and Entomorphthora.

DETAILED EXPLANATION

The present invention was completed on the basis of the above findings. Namely, the present invention relates to domestic fowl eggs having a high content of arachidonic acid and optionally docosahexaenoic acid, and a process for production thereof comprising feeding egg-laying domestic fowls with ω6 highly unsaturated fatty acid and optionally ω3 highly unsaturated fatty acid, as well as lipid having a high content of arachidonic acid and optionally docosahexaenoic acid obtained by extracting from the resulting domestic fowl eggs, and particularly the yolks, a process for production thereof, and the use thereof.

The egg-laying domestic fowls used in the present invention may be any of the large number of types of fowl referred to as poultry provided their eggs are edible, examples of which include chickens, quail, ducks and crossbreeds of wild and domestic ducks.

The ω6 highly unsaturated fatty acid of the present invention is that having at least 18 carbon atoms, preferably at least 20 carbon atoms, and at least 3 double bonds which start from the 6th carbon atom counting from the carbon atom on the methyl group terminal of the fatty acid, examples of which include γ-linolenic acid, dihomo-γ-linolenic acid and arachidonic acid. Although these fatty acids can be used either alone or as a mixture, it is preferable that they include at least arachidonic acid. In addition, these fatty acids can be added in various forms. Examples of these forms include salts, atoxic metal salts, for example, alkaline metal salts such as sodium salts and potassium salts, alkaline earth metal salts such as calcium salts and magnesium salts, ammonium salts, esters such as methylesters, ethylesters and propylesters, triacylglycerols, diacylglycerols, monoacylglycerols, glyerophospholipids, glyceroglycolipids, sphingophospholipids and sphingoglycolipids.

The ω6 highly unsaturated fatty acids of the present invention may be chemically synthesized, or derived from an animal, plant or microorganism and so forth that contains ω6 highly unsaturated fatty acid, or that which is isolated, extracted, purified or is a residue thereof, an example of which is an oil or extract residue obtained from a microorganism having an ability to produce arachidonic acid. In addition, it is desirable that the oil containing ω6 highly unsaturated fatty acid of the present invention contains at least 5.5%, preferably at least 10%, and more preferably at least 20% arachidonic acid with respect to total fatty acids.

Moreover, in the present invention, the ω6 highly unsaturated fatty acid can be used in combination with other fatty acids such as linoleic acid, ω3 highly unsaturated fatty acids and so forth.

The ω3 highly unsaturated fatty acid has at least 18 carbon atoms and at least 2 double bonds which start from the 3rd carbon atom counting from the carbon atom of the methyl group terminal of the fatty acid. Examples of the ω3 highly unsaturated fatty acid used in the present invention are α-linolenic acid, 8,11,14,17-eicosatetraenoic acid, 5,8,11,14,17-eicosapentaenoic acid, 7,10,13,16,19-docosapentaenoic acid and 4,7,10,13,16,19-docosahexaenoic acid. For the sake of brevity, the double bond locations will be omitted. In addition, these fatty acids can be added in various forms.

Examples of forms in which the above-mentioned fatty acids can be added include salts, atoxic metal salts, for example, alkaline metal salts such as sodium salts and potassium salts, alkaline earth metal salts such as calcium salts and magnesium salts, ammonium salts, esters such as methylesters, ethylesters and propylesters, triacylglycerols, diacylglycerols, monoacylglycerols, glycerophospholipids, glyceroglycolipids, sphingophospholipids and sphingoglycolipids.

The ω3 highly unsaturated fatty acids of the present invention may be chemically synthesized or derived from an animal, plant or microorganism and so forth that contains ω3 highly unsaturated fatty acid, or that which is isolated, extracted or purified therefrom, examples of which include fish oil, fish powder, fish refuse, fish oil extract, an oil or extract residue obtained from microorganisms having an ability to produce docosahexanoic acid and so forth.

Typical examples of fish oils include sardine oil, herring oil, tuna oil, bonito oil, saury oil and menherden oil. Although there are no particular limitations on the type of fish oil used in the present invention, since the fatty acid composition in the oil varies according to the type of fish, selecting and using a fish oil having a high content of docosahexaenoic acid and a low content of eicosapentaenoic acid is preferable for obtaining eggs having a low content of eicosapentaenoic acid.

In the present invention, all microorganisms can be used provided they have an ability to produce arachidonic acid or docosahexaenoic acid. Examples of microorganisms having an ability to produce arachidonic acid include those of the genus Mortierella, Conidiobolus, Phythium, Phytophthora, Penicillium, Cladosporium, Mucor, Fusarium, Aspergillus, Rhodotorula, Entomophthora, Echinosporangium and Saprolegnia.

In the case of the genus Mortierella, microorganisms belonging to the genus Mortierella, subgenus Mortierella can be used, examples of which include *Mortierella elongata* IFO 8570, *Mortierella exiqua* IFO 8571, *Mortierella hygrophila* IFO 5941 and *Mortierella alpina* IFO 8568. All of these strains can be acquired without restriction from the Institute for Fermentation Osaka. In addition, the present inventions can also use *Mortierella elongata* SAM 0219 (FERM P-8703) (FERM BP-1239).

*Mortierella alpina* is particularly preferable in the present invention because it intracellularly accumulates a large amount of arachidonic acid. In addition, since this microorganism produces hardly eicosapentaenoic acid at normal temperatures (preferably 20 to 30° C.), it is suited extremely well for obtaining eggs having a low content of eicosapentaenoic acid. Examples of *Mortierella alpina* other than that listed above include *Mortierella alpina* ATCC 16266, ATCC 42430, ATCC 32221, CBS219.35, CBS224.37, CBS250.53, CBS343.66, CBS527.72, CBS529.72, CBS608.70 and CBS754.68.

Examples of microorganisms that have an ability to produce docosahexaenoic acid include members of the phylum Chromophycota, such as of the genus Crypthecodimium, Isochrysis, Nanochloropsis, Chaetoceros, Phaeodactylum, Amphidinium, Gonyaulax, Peridimium, Chroomonas, Cryptomonas, Hemiselmis, Chilomonas, as well as members of the phylum of Chlorophycota such as of the genus Chlorella, Histiobranchus, Coryphaenoides, Thraustchytrium, Schizochytrium Conidiobolus and Entomorphthora. Examples of Crypthecodimium include *Crypthecodimium cohnii* ATCC 30021, while examples of Thraustchytrium include *Thraustchytrium aureum* ATCC 34304. These strains can be acquired without restriction from the American Type Culture Collection.

Microorganisms having an ability to produce arachidonic acid or microorganisms having an ability to produce docosahexaenoic acid can be cultured in accordance with routine methods. For example, the spores, mycelia or pre-culture liquid obtained by culturing in advance of said microorganism can be cultured by inoculating into liquid medium or solid medium. An oil containing highly unsaturated fatty acid such as arachidonic acid or docosahexaenoic acid is intracellularly accumulated as a result of culturing.

Following completion of culturing, cultured microbial cells are obtained from the culture by commonly employed solid-liquid separation techniques such as centrifugal separation and filtration. Dry microbial cells are obtained by washing the cultured microbial cells with an ample amount of water and then drying. Drying can be performed by freeze-drying, spray drying and so forth. The dried microbial cells are preferably extracted with organic solvent in the presence of a nitrogen gas. Examples of organic solvents that can be used include ethyl ether, hexane, methanol, ethanol, chloroform, dichloromethane, petroleum ether and acetone. In addition, favorable results can also be obtained by alternating extraction with methanol and petroleum ether or by extraction using a single-layer solvent of chloroform, methanol and water. An oil can then be obtained containing highly unsaturated fatty acid such as arachidonic acid or docosahexaenoic acid by distilling off the organic solvent from the extract under a reduced pressure.

According to the present invention, in the case of feeding domestic fowls with oil derived from microorganisms having an ability to produce arachidonic acid or oil derived from microorganisms having an ability to produce docosahexaenoic acid, in addition to the oil extracted from cultured microbial cells, the oil can be fed in forms including culture liquid taken during the course of culturing or that sterilized culture liquid, culture liquid taken at completion of culturing or that sterilized culture liquid, cultured microbial cells collected from those respective culture liquids or those dried microbial cells, or residue obtained after extracting oil from the microbial cells.

There are no particular limitations on the manner in which domestic fowls are fed with ω6 highly unsaturated fatty acid and optionally ω3 highly unsaturated fatty acid. For example, these highly unsaturated fatty acids can be added to feed, or given in drinking water followed by emulsification using O/W emulsifier, to a concentration of 0.1–3% by weight (Japanese Unexamined Patent Publication No. 60-105471) or subcutaneously administered (Japanese Unexamined Patent Publication No. 5-292583). In addition, in order to produce the domestic fowl eggs of the present invention, it is preferable to feed said domestic fowls witht the fatty acids at a dose of at least 100 mg/day/fowl, and preferably at least 400 mg/day/fowl. Although merely adding ω6 highly unsaturated fatty acid and optionally ω3 highly unsaturated fatty acid in feed is the simplest method, since its oxidation cannot be avoided, there are problems in terms of its quality control as well as the generation of a foul odor in the vicinity of the breeding area.

However, in the case of using microorganisms that have an ability to produce arachidonic acid or microorganisms that have an ability to produce docosahexaenoic acid, although problems similar to those above occur in the case of adding its extracted oil to feed, in the case of using the microbial cells of these microorganisms, the oil in the microbial cells is stable and, there are immeasurable advantages in terms of costs, since the extraction procedure can be omitted, as well as in terms of being able to provide other nutrients (proteins, sugars and so forth).

With the exception of trace amounts contained in the egg white and egg shell, virtually all of the lipid in domestic fowl eggs is contained in the yolk, and the majority of this egg yolk lipid is said to be bound to protein. Thus, in the case of extracting lipid from yolk, the amount and composition of the extracted lipid varies according to the type of solvent used and extraction conditions. If the egg yolk is treated in advance using enzyme (protease preparation containing lipase), an amount of lipid extracted by solvent extraction increases. Examples of typically used effective extraction agents include a mixture of ethanol and ether (3:1) and a mixture of chloroform and methanol (1:1), and these solvents are suited for extraction of all yolk lipids. In addition, by first freeze-drying the yolk in advance to form a powder, and then extracting with a mixture of chloroform and methanol, lipid is completely extracted. In particular, ethanol or hexane alone, a mixture of ethanol and hexane or a mixture of ethanol and water are preferable since they are solvents suitable for use in foods.

Fatty acid analysis can be performed in accordance with routine methods. For example, fatty acids can be measured by gas chromatography, high-performance liquid chromatography and so forth.

The egg yolk lipid of the present invention thus obtained is richer in arachidonic acid than conventional eggs. More specifically, this egg yolk lipid contains at least 2%, preferably at least 2.7%, and more preferably at least 3% arachidonic acid with respect to the total fatty acids contained in the egg yolk. In addition, in the present invention, fatty acid analysis of the resulting lipid having a high content of arachidonic acid and docosahexaenoic acid indicates a ratio of 1 to 12 parts by weight of docosahexaenoic acid to 1 to 12 parts by weight of arachidonic acid. Moreover, said egg yolk lipid is characterized by demonstrating a ratio of at least 5 parts by weight of arachidonic acid to 1 part by weight of eicosapentaenoic acid.

Therefore, the lipid of the present invention having a high content of arachidonic acid and optionally docosahexaenoic acid extracted from domestic fowl eggs, and particularly the egg yolks, obtained by feeding egg-laying domestic fowls with ω6 highly unsaturated fatty acid and optionally ω3 highly unsaturated fatty acid has a low ratio of eicosahexaenoic acid with respect to total fatty acids in the egg yolk even in the case the above-mentioned domestic fowls are raised using fish oil for the ω3 highly unsaturated fatty acid. Thus, an extracted lipid is obtained that has high ratios of arachidonic acid and optionally docosahexaenoic acid, which can be effectively used in formula for premature infants, infant formula, a follow-up formula or as a milk product for expectance or nursing mother. Namely, a powdered formula that is closer to natural mother's milk can be obtained by adding an oil extracted from domestic fowl eggs, and particularly the yolks, obtained by feeding egg-laying domestic fowls with ω6 highly unsaturated fatty acid and optionally ω3 highly unsaturated fatty acid, to the production process or finished formula such as dietary formula to premature infants, dietary formula to infants, a follow-up formula or milk product for expectant nursing mothers.

The types of foods to which is added lipid having a high content of arachidonic acid and optionally docosahexaenoic acid extracted from domestic fowl eggs of the present invention are not limited to formula for premature infants, formula for nursing infants, follow-up formula or milk product for expectant or nursing mothers. One example is the addition to foods containing oils, examples of which include natural foods containing oils of meat, fish and nuts, foods to which oils are added during preparation such as Chinese food, Chinese noodles and soup, foods using oil as a heat medium such as tempura, deep-fried fish, deep-fried bean curd, fried rice, doughnuts and deep-fried confections, oily foods or processed foods to which oils are added during processing such as butter, margarine, mayonnaise, salad dressing, chocolate, instant Chinese noodles, caramel, cookies and ice cream, as well as foods that are sprayed or coated with oil during final processing such as crackers, hard biscuits and jam-filled bread.

However, examples are not limited to foods containing oil, but rather also include agricultural foods such as bread, noodles, rice, confections, bean curd and their processed foods, fermented foods such as rice wine and medicinal liquors, livestock foods such as sweet rice wine, vinegar, soy sauce, miso, salad dressing, yogurt, ham, bacon, sausage and mayonnaise, sea foods such as boiled fish paste, deep-fried fish and fish cake, as well as beverages such as fruit juice, soft drinks, sports drinks, alcoholic beverages and tea.

Although there are no particular limitations on the used amount of lipid having a high content of arachidonic acid and optionally docosahexaenoic acid extracted from domestic fowl eggs of the present invention, at least 0.001% preferably at least 0.1%, and more preferably at least 1% by weight is contained with respect to the food product to which it is added. The following provides a detailed explanation of the present invention through its embodiments.

EXAMPLES

Example 1

Production of Arachidonic Acid Using Microorganisms Having Ability to Produce Arachidonic Acid Using *Mortierella alpina* IFO 8568 for an arachidonic acid-producing microorganism, medium (1400 L) containing 2% glucose, 1% yeast extract and 0.1% soybean oil was placed in a 2000 L fermentor followed by aeration stirring culturing for 7 days under conditions of a temperature of 28° C., aeration volume of 1.0 vvm and agitation of 80 rpm. Dried powdered microbial cells were prepared following completion of culturing. As a result, 26.7 kg of dried microbial cells were obtained containing 60% oil having a high content of ω6 highly unsaturated fatty acids (3.0% γ-linolenic acid, 2.7% dihomo-γ-linolenic acid, 24.1% arachidonic acid (ω6 highly unsaturated fatty acids:ω3 highly unsaturated fatty acids=29.8:1).

Example 2

Production of Docosahexaenoic Acid Using Microorganisms Having Ability to Produce Docosahexaenoic Acid Using *Crypthecodimium cohnii* ATCC30021 for docosahexaenoic acid-producing microorganism, 6.8 L of concentrated yeast extract (400 g/l) and 12.5 L of glucose syrup (400 g/l) were added to artificial seawater culture liquid diluted to one-half concentration prepared by combining 4.3 kg of I.O. and 230 L of tap water followed by culturing for 76 hours under conditions of a temperature of 28° C., aeration volume of 1.0 vvm and terminal speed of 73 cm/second. Following completion of culturing, the algae cells were acquired by centrifugation and after washing the cells with water, were freeze-dried to prepare dried microbial cells. As a result, microbial cells were obtained containing 20% oil having a high content of ω3 highly unsaturated fatty acids (35.0% docosahexaenoic acid).

Example 3

Production of Eggs Having High Content of ω6 Highly Unsaturated Fatty Acid (1)

Isa Brown, 200-day-old, egg-laying chickens were divided into two groups of 30 chickens each. The first group was treated as the control group and fed with ordinary feed for 33 days. The other group was treated as the test group, namely the ω6 highly unsaturated fatty acid dose group, and fed with feed in which was mixed the dried microbial cells obtained in Example 1 so that a total of 5 g were ingested daily (3 g as oil having a high content of ω6 highly unsaturated fatty acid).

The egg weight (g), yolk weight (g), yolk content (%), extracted oil weight (g), ratio of arachidonoic acid to total fatty acids (%), ratio of eicosapentaenoic acid to total fatty acids (%), and ratio of docosahexaenoic acid to total fatty acids (%) were determined for 3 eggs over time. Those results are shown in Table 1. Furthermore, the eggs that were obtained were frozen, and after denaturing the protein, were dried at high frequency to form chips measuring 5–10 mm on a side (yield: 45%). 1000 ml of ethanol was added to 300 g of these chips, extracted for 2 hours at 60 to 70° C. and then filtered to obtain a filtrate. Moreover, 800 ml of ethanol was added to the filtration residue followed by additional extraction for 2 hours at 60 to 70° C. and filtration. The first and second filtrates were combined after which the ethanol was removed by a rotary evaporator (vacuum: 30 mmHg, 60–70° C.). Finally, molecular distillation was performed by circulating for 2 hours at 60° C. and $10^{-3}$ mmHg to completely remove ethanol. 150 g of yolk oil were obtained equal to roughly half of the 300 g of chips. The ratio of ω6 highly unsaturated fatty acids (and particularly arachidonic acid) to total lipid in the yolk was clearly increased by feeding the chickens with ω6 highly unsaturated fatty acids. Moreover, since ω3 highly unsaturated fatty acids consisted almost entirely of docosahexaenoic acid, this oil is even more suitable in the case of using the extracted oil in powdered milk product for premature infants and powdered milk product for nursing infants.

TABLE 1

| Group | Item | No. of Days | | | | | | | |
|---|---|---|---|---|---|---|---|---|---|
| | | 0 | 5 | 10 | 16 | 20 | 25 | 30 | 33 |
| Control Group | Egg weight (3 eggs) g | 201.4 | 195.8 | 198.8 | 204.1 | 211.0 | 199.4 | 213.1 | 210.4 |
| | Yolk weight g | 49.6 | 50.1 | 51.2 | 52.7 | 53.9 | 50.3 | 55.1 | 51.4 |
| | Yolk content % | 24.6 | 25.6 | 25.7 | 25.8 | 25.4 | 25.2 | 25.9 | 24.4 |
| | Extracted oil weight g | 14.2 | 13.4 | 14.4 | 12.8 | 16.1 | 15.1 | 14.5 | 15.9 |
| | Arachidonic acid % | 1.6 | 1.7 | 1.3 | 1.4 | 1.3 | 1.6 | 1.8 | 1.5 |
| | Eicosapentaenoic acid % | trace | trace | trace | trace | trace | trace | trace | trace |
| | Docosahexaenoic acid % | 1.7 | 1.5 | 1.6 | 1.8 | 1.7 | 1.7 | 1.5 | 1.8 |
| Test Group | Egg weight (3 eggs) g | 198.5 | 188.5 | 183.1 | 194.6 | 201.7 | 206.1 | 200.8 | 199.4 |
| | Yolk weight g | 48.3 | 47.1 | 45.7 | 47.6 | 49.8 | 52.6 | 50.3 | 49.9 |
| | Yolk content % | 24.3 | 25.0 | 25.0 | 24.5 | 24.7 | 25.5 | 25.0 | 25.0 |
| | Extracted oil weight g | 13.7 | 14.7 | 16.1 | 13.1 | 14.4 | 15.8 | 14.3 | 13.8 |
| | Arachidonic acid % | 1.7 | 2.4 | 3.6 | 3.9 | 4.0 | 3.7 | 4.3 | 3.6 |
| | Eicosapentaenoic acid % | trace | trace | trace | trace | trace | trace | trace | trace |
| | Docosahexaenoic acid % | 1.3 | 1.4 | 1.6 | 1.5 | 1.7 | 1.3 | 1.4 | 1.6 |

Example 4

Production of Eggs Having High Content of ω6 Highly Unsaturated Fatty Acid (2)

Isa Brown, 200-day-old, egg-laying chickens were divided into two groups of 30 chickens each. The first group was treated as the control group and fed with ordinary feed for 33 days. The other group was treated as the test group, namely the ω6 highly unsaturated fatty acid dose group.

The test group was fed for 33 days with a mixture of feed and dried microbial cells containing 60% of the oil having a high content of ω6 highly unsaturated fatty acids (3.2% γ-linolenic acid, 4.4% dihomo-γ-linolenic acid, 39.0% arachidonic acid (ω6 highly unsaturated fatty acids:ω3 highly unsaturated fatty acids=269.5:1)) obtained using *Mortierella alpina* CBS 210.32 as an arachidonic acid-producing microorganism in accordance with the production process of arachidonic acid using microorganisms described in Example 1, so that 5 g were ingested per day.

The egg weight (g), yolk weight (g), yolk content (%), extracted oil weight (g), ratio of arachidonic acid to total fatty acid (%), ratio of eicosapentaenic acid to total fatty acid (%), and ratio of docosahexaenoic acid to total fatty acid (%) were determined for 3 eggs over time. Those results are shown in Table 2. Furthermore, yolk oil was obtained using the same procedure as described in Example 3. The ratio of ω6 highly unsaturated fatty acids (and particularly arachidonic acid) to total lipid in the yolk was clearly increased by feeding the chickens ω6 highly unsaturated fatty acid.

Moreover, since ω3 highly unsaturated fatty acids consisted almost entirely of docosahexaenoic acid, this oil is even more suitable in the case of using the extracted oil in powdered milk product for premature infants and powdered milk product for nursing infants.

namely the ω6 highly unsaturated fatty acid and ω3 highly unsaturated fatty acid dose group, and fed for 33 days with a mixture of ordinary feed, the dried microbial cells obtained in Example 1 and fish oil so as to ingest 5 g per day of the dried microbial cells (3 g as oil having a high content of ω6 highly unsaturated fatty acids) and 3 g per day of fish oil (trace α-linolenic acid, 4.1% docosapentaenoic acid, 4.8% eicosapentaenoic acid, 21.8% docosahexaenoic acid) (ω6 highly unsaturated fatty acids:ω3 highly unsaturated fatty acids=1:30.7).

The chicken body weight (g), yolk weight (g), yolk content (%), extracted oil weight (g), ratio of arachidonic acid to total fatty acid (%), ratio of eicosapentaenoic acid to

TABLE 2

| Group | Item | No. of Days | | | | | | | |
|---|---|---|---|---|---|---|---|---|---|
| | | 0 | 5 | 10 | 16 | 20 | 25 | 30 | 33 |
| Control Group | Egg weight (3 eggs) g | 201.4 | 195.8 | 198.8 | 204.1 | 211.0 | 199.4 | 213.1 | 210.4 |
| | Yolk weight g | 49.6 | 50.1 | 51.2 | 52.7 | 53.9 | 50.3 | 55.1 | 51.4 |
| | Yolk content % | 24.6 | 25.6 | 25.7 | 25.8 | 25.4 | 25.2 | 25.9 | 24.4 |
| | Extracted oil weight g | 14.2 | 13.4 | 14.4 | 12.8 | 16.1 | 15.1 | 14.5 | 15.9 |
| | Arachidonic acid % | 1.6 | 1.7 | 1.3 | 1.4 | 1.3 | 1.6 | 1.8 | 1.5 |
| | Eicosapentaenoic acid % | trace | trace | trace | trace | trace | trace | trace | trace |
| | Docosahexaenoic acid % | 1.7 | 1.5 | 1.6 | 1.8 | 1.7 | 1.7 | 1.5 | 1.8 |
| Test Group | Egg weight (3 eggs) g | 197.3 | 199.1 | 201.5 | 203.7 | 198.2 | 204.6 | 211.0 | 206.2 |
| | Yolk weight g | 48.5 | 49.2 | 51.4 | 52.3 | 50.9 | 53.5 | 52.0 | 53.2 |
| | Yolk content % | 25.1 | 26.3 | 27.0 | 26.2 | 26.1 | 25.3 | 24.9 | 25.7 |
| | Extracted oil weight g | 14.2 | 15.2 | 14.8 | 14.1 | 13.8 | 14.8 | 15.9 | 14.7 |
| | Arachidonic acid % | 0.7 | 2.1 | 7.9 | 8.1 | 8.0 | 8.2 | 8.3 | 8.1 |
| | Eicosapentaenoic acid % | trace | trace | trace | trace | trace | trace | trace | trace |
| | Docosahexaenoic acid % | 1.6 | 1.4 | 1.8 | 1.6 | 1.6 | 1.5 | 1.3 | 1.4 |

Example 5

Production of Eggs Having High Content of ω6 Highly Unsaturated Fatty Acid and ω3 Highly Unsaturated Fatty Acid (1)

Isa Brown, 200-day-old, egg-laying chickens were divided into two groups of 30 chickens each. The first group was treated as the control group and fed with ordinary feed for 33 days. The other group was treated as the test group, total fatty acid (%), and ratio of docosahexaenoic acid to total fatty acid (%) were determined for 3 eggs over time. Those results are shown in Table 3. Furthermore, yolk oil was obtained using the same procedure as described in Example 3. The ratio of ω6 highly unsaturated fatty acids (and particularly arachidonic acid) and ω3 highly unsaturated fatty acids (and particularly docosahexaenoic acid) to total lipid in the yolk was clearly increased by feeding the chickens with ω6 highly unsaturated fatty acids and ω3 highly unsaturated fatty acids.

TABLE 3

| Group | Item | No. of Days | | | | | | | |
|---|---|---|---|---|---|---|---|---|---|
| | | 0 | 5 | 10 | 16 | 20 | 25 | 30 | 33 |
| Control Group | Egg weight (3 eggs) g | 201.4 | 195.8 | 198.8 | 204.1 | 211.0 | 199.4 | 213.1 | 210.4 |
| | Yolk weight g | 49.6 | 50.1 | 51.2 | 52.7 | 53.9 | 50.3 | 55.1 | 51.4 |
| | Yolk content % | 24.6 | 25.6 | 25.7 | 25.8 | 25.4 | 25.2 | 25.9 | 24.4 |
| | Extracted oil weight g | 14.2 | 13.4 | 14.4 | 12.8 | 16.1 | 15.1 | 14.5 | 15.9 |
| | Arachidonic acid % | 1.6 | 1.7 | 1.3 | 1.4 | 1.3 | 1.6 | 1.8 | 1.5 |
| | Eicosapentaenoic acid % | trace | trace | trace | trace | trace | trace | trace | trace |
| | Docosahexaenoic acid % | 1.7 | 1.5 | 1.6 | 1.8 | 1.7 | 1.7 | 1.5 | 1.8 |
| Test Group | Egg weight (3 eggs) g | 195.5 | 186.6 | 203.8 | 205.7 | 190.4 | 212.4 | 212.7 | 206.5 |
| | Yolk weight g | 49.9 | 51 | 52.2 | 49.2 | 50.4 | 56.6 | 52.3 | 51.7 |
| | Yolk content % | 25.5 | 27.3 | 25.6 | 23.9 | 26.5 | 26.6 | 24.6 | 25 |
| | Extracted oil weight g | 13.2 | 15.2 | 13.1 | 12.4 | 11.4 | 13.2 | 16.3 | 14.8 |
| | Arachidonic acid % | 0.74 | 1.75 | 3.1 | 4.04 | 3.2 | 4.3 | 3.9 | 3.1 |
| | Eicosapentaenoic acid % | trace | trace | trace | trace | trace | trace | trace | trace |
| | Docosahexaenoic acid % | 1.3 | 2.1 | 3.4 | 3.6 | 4.3 | 3.8 | 4.2 | 4.1 |

Moreover, although a high proportion of eicosapentaenic acid is contained in the fish oil, in the present Example in which fish oil is used for the ω3 highly unsaturated fatty acids, the ratio of eicosapentaenoic acid to total lipid in the yolk can be held to less than that of docosahexaenoic acid.

Example 6

Production of Eggs Having High Content of ω6 Highly Unsaturated Fatty Acid and ω3 Highly Unsaturated Fatty Acid (2)

Isa Brown, 200-day-old, egg-laying chickens were divided into two groups of 30 chickens each. The first group was treated as the control group and fed with ordinary feed for 33 days. The other group was treated as the test group, namely the ω6 highly unsaturated fatty acid and ω3 highly unsaturated fatty acid dose group, and fed for 33 days with a mixture of ordinary feed, the dried microbial cells obtained in Example 1 and the dried microbial cells obtained in Example 2 so as to ingest 5 g per day of the dried microbial cells of Example 1 (3 g as oil having a high content of ω6 highly unsaturated fatty acids) and 10 g per day of the dried microbial cells of Example 2 (2 g as oil having a high content of ω3 highly unsaturated fatty acids).

The egg weight (g), yolk weight (g), yolk content (%), extracted oil weight (g), ratio of arachidonic acid to total fatty acid (%), ratio of eicosapentaenoic acid to total fatty acid (%), and ratio of docosahexaenoic acid to total fatty acid (%) were determined for 3 eggs over time. Those results are shown in Table 4. Furthermore, yolk oil was obtained using the same procedure as described in Example 3. The ratio of ω6 highly unsaturated fatty acids (and particularly arachidonic acid) and ω3 highly unsaturated fatty acids (and particularly docosahexaenoic acid) to total lipid in the yolk was clearly increased by feeding the chickens with ω6 highly unsaturated fatty acids and ω3 highly unsaturated fatty acids.

divided into two groups of 30 chickens each. The first group was treated as the control group and fed with ordinary feed for 33 days. The other group was treated as the test group, namely the ω6 highly unsaturated fatty acid and ω3 highly unsaturated fatty acid dose group.

The test group was fed for 33 days with a mixture of feed, dried microbial cells containing 60% oil having a high content of ω6 highly unsaturated fatty acids (3.2% γ-linolenic acid, 4.4% dihomo-γ-linolenic acid, 39.0% arachidonic acid (ω6 highly unsaturated fatty acids:ω3 highly unsaturated fatty acids=269.5:1)), obtained using *Mortierella alpina* CBS 210.32 for the arachidonic acid-producing mold in accordance with the production process of arachidonic acid using microorganisms described in Example 1, and fish oil (trace α-linolenic acid, 4.1% docosapentaenoic acid, 4.8% eicosapentaenoic acid, 21.8% docosahexaenoic acid (ω6 highly unsaturated fatty acids:ω3 highly unsaturated fatty acids=1:30.7)) so that 5 g per day of the oil and 3 g per day of fish oil were ingested.

The egg weight (g), yolk weight (g), yolk content (%), extracted oil weight (g), ratio of arachidonoic acid to total fatty acid (%), ratio of eicosapentaenoic acid to total fatty acid (%), and ratio of docosahexaenoic acid to total fatty acid (%) were determined for 3 eggs over time. Those results are shown in Table 5. Furthermore, yolk oil was obtained using the same procedure as described in Example 3. The ratio of ω6 highly unsaturated fatty acids (and particularly arachidonic acid) and ω3 highly unsaturated fatty acids (and particularly docosahexaenoic acid) to total lipid in the yolk was clearly increased by feeding the chickens with ω6 highly unsaturated fatty acids and ω3 highly unsaturated fatty acids.

TABLE 4

| Group | Item | \multicolumn{8}{c}{No. of Days} |
|---|---|---|---|---|---|---|---|---|---|
| | | 0 | 5 | 10 | 16 | 20 | 25 | 30 | 33 |
| Control Group | Egg weight (3 eggs) g | 201.4 | 195.8 | 198.8 | 204.1 | 211.0 | 199.4 | 213.1 | 210.4 |
| | Yolk weight g | 49.6 | 50.1 | 51.2 | 52.7 | 53.9 | 50.3 | 55.1 | 51.4 |
| | Yolk content % | 24.6 | 25.6 | 25.7 | 25.8 | 25.4 | 25.2 | 25.9 | 24.4 |
| | Extracted oil weight g | 14.2 | 13.4 | 14.4 | 12.8 | 16.1 | 15.1 | 14.5 | 15.9 |
| | Arachidonic acid % | 1.6 | 1.7 | 1.3 | 1.4 | 1.3 | 1.6 | 1.8 | 1.5 |
| | Eicosapentaenoic acid % | trace | trace | trace | trace | trace | trace | trace | trace |
| | Docosahexaenoic acid % | 1.7 | 1.5 | 1.6 | 1.8 | 1.7 | 1.7 | 1.5 | 1.8 |
| Test Group | Egg weight (3 eggs) g | 190.5 | 195.8 | 201.9 | 210.3 | 198.7 | 197.5 | 207.5 | 212.4 |
| | Yolk weight g | 45.3 | 48.2 | 51.3 | 53.5 | 50.2 | 50.1 | 52.6 | 49.7 |
| | Yolk content % | 23.8 | 24.6 | 25.4 | 25.4 | 25.3 | 25.4 | 25.3 | 23.4 |
| | Extracted oil weight g | 14.1 | 15.6 | 13.9 | 14.3 | 16.1 | 14.0 | 15.7 | 16.3 |
| | Arachidonic acid % | 1.8 | 2.3 | 3.2 | 3.9 | 4.2 | 3.9 | 4.1 | 3.6 |
| | Eicosapentaenoic acid % | trace | trace | trace | trace | trace | trace | trace | trace |
| | Docosahexaenoic acid % | 1.5 | 1.9 | 3.3 | 4.1 | 3.9 | 4.2 | 4.0 | 3.6 |

Example 7

Production of Eggs Having High Content of ω6 Highly Unsaturated Fatty Acid and ω3 Highly Unsaturated Fatty Acid (3)

Isa Brown, 200-day-old, egg-laying chickens were

Moreover, in the case of using fish oil for the ω3 highly unsaturated fatty acids, although a high proportion of eicosapentaenic acid is contained in the fish oil, when given as feed, hardly any eicosapentaenic acid was contained in the egg yolks.

TABLE 5

| Group | Item | No. of Days | | | | | | | |
|---|---|---|---|---|---|---|---|---|---|
| | | 0 | 5 | 10 | 16 | 20 | 25 | 30 | 33 |
| Control Group | Egg weight (3 eggs) g | 201.4 | 195.8 | 198.8 | 204.1 | 211.0 | 199.4 | 213.1 | 210.4 |
| | Yolk weight g | 49.6 | 50.1 | 51.2 | 52.7 | 53.9 | 50.3 | 55.1 | 51.4 |
| | Yolk content % | 24.6 | 25.6 | 25.7 | 25.8 | 25.4 | 25.2 | 25.9 | 24.4 |
| | Extracted oil weight g | 14.2 | 13.4 | 14.4 | 12.8 | 16.1 | 15.1 | 14.5 | 15.9 |
| | Arachidonic acid % | 1.6 | 1.7 | 1.3 | 1.4 | 1.3 | 1.6 | 1.8 | 1.5 |
| | Eicosapentaenoic acid % | trace | trace | trace | trace | trace | trace | trace | trace |
| | Docosahexaenoic acid % | 1.7 | 1.5 | 1.6 | 1.8 | 1.7 | 1.7 | 1.5 | 1.8 |
| Test Group | Egg weight (3 eggs) g | 198.2 | 199.1 | 204.8 | 203.1 | 194.5 | 211.7 | 212.7 | 203.3 |
| | Yolk weight g | 49.9 | 51.2 | 52.4 | 49.3 | 50.1 | 54.4 | 52.3 | 53.5 |
| | Yolk content % | 24.8 | 26.6 | 27.1 | 25.9 | 25.4 | 26.6 | 24.8 | 25.9 |
| | Extracted oil weight g | 14.3 | 15.5 | 14.8 | 13.9 | 12.7 | 13.2 | 15.9 | 14.8 |
| | Arachidonic acid % | 0.7 | 2.2 | 8.0 | 8.1 | 8.1 | 8.2 | 8.2 | 8.3 |
| | Eicosapentaenoic acid % | trace | trace | trace | trace | trace | trace | trace | trace |
| | Docosahexaenoic acid % | 1.5 | 2.1 | 3.3 | 4.2 | 3.9 | 4.1 | 4.0 | 4.3 |

Example 8

Preparation of Formula Containing Oil Having a High Content of Arachidonic Acid

A formula suitable for feeding infants having a high content of arachidonic acid was prepared by mixing 1 g of the oil having a high content of arachidonic acid obtained in Example 3 into 100 g of formula material. The ratio of arachidonic acid to total fatty acids of this formula was 0.16%, thus enabling the amount of arachidonic acid lacking in conventional infant formula to approach that of natural mother's milk.

Example 9

Preparation of Formula Containing Oil Having High Content of Highly Unsaturated Fatty Acid A formula suitable for feeding infants having a high content of arachidonic acid and docosahexaenoic acid was prepared by mixing 1 g of the oil having a high content of arachidonic acid and docosahexaenoic acid (4.0% arachidonic acid, trace eicosapentaenoic acid, 4.1% docosahexaenoic acid) obtained from eggs obtained in Example 5 into 100 g of formula material. The ratios of arachidonic acid, eicosapentaenoic acid and docosahexaenoic acid to total fatty acids of this formula product were 0.16%, trace, and 0.16%, respectively, thus enabling the amounts of arachidonic acid and docosahexaenoic acid lacking in conventional infant formula to approach those of natural mother's milk.

What is claimed is:

1. Domestic fowl eggs having at least 3% arachidonic acid with respect to total fatty acids contained in an egg yolk and optionally docosahexaenoic acid, wherein said domestic fowl eggs are obtained by feeding egg-laying domestic fowls with at least one ω6 highly unsaturated fatty acid selected from the group consisting of dihomo-γ-linolenic acid and arachidonic acid and optionally ω3 highly unsaturated fatty acid.

2. Domestic fowl eggs according to claim 1 wherein the ω6 highly unsaturated fatty acid is at least one fatty acid selected from the group consisting, dihomo-γ-linolenic acid and arachidonic acid, that is used in at least one form selected from the group consisting of free fatty acid, salt, ester, triacylglycerol, diacylglycerol, monoacylglycerol, glycerophospholipid, glycerolycolipid, shingophospholipid and sphingoglycolipid.

3. Domestic fowl eggs according to claim 1 obtained by feeding said ω6 highly unsaturated fatty acid either alone or as a mixture in the form of (1) an oil or extract residue obtained by extracting from dried microbial cells or wet microbial cells of a microorganism having an ability to produce arachidonic acid or (2) dried or wet microbial cells of a microorganism having an ability to produce arachidonic acid.

4. Domestic fowl eggs according to claim 3 wherein the microorganism having an ability to produce arachidonic acid is of the genus Mortierella, Conidiobolus, Pythium, Phytophthora, Penicillium, Cladosporium, Mucor, Fusarium, Aspergillus, Rhodotorula, Entomophthora, Echinosporangium or Saprolegnia.

5. Domestic fowl eggs according to claim 1 wherein the ω3 highly unsaturated fatty acid is present and is at least one fatty acid selected from the group consisting of α-linolenic, 8,11,14,17-eicosatetraenoic acid, eicosapentaenoic acid, docosapentaenoic acid and docosahexaenoic acid, that is used in at least one form selected from the group consisting of free fatty acid, salt, ester, triacylglycerol, diacylglycerol, monoacylglycerol, glyerophospholipid, glyceroglycolipid, spingophospholipid and sphingoglycolipid.

6. Domestic fowl eggs according to claim 1 obtained by feeding said ω3 highly unsaturated fatty acid either alone or as a mixture in the form of fish oil, fish powder, fish refuse, fish oil extract, an oil or extract residue obtained by extracting from dried or wet microbial cells of microorganism having the ability to produce docosahexaenoic acid, or dried or wet microbial cells of microorganism having the ability to produce docosahexaenoic acid.

7. Domestic fowl eggs according to claim 6 wherein the microorganism having the ability to produce docosahexaenoic acid is of the genus Crypthecodimium, Isochrysis, Nanochloropsis, Chaetoceros, Phaeodactylum, Amphidinium, Gonyaulax, Peridimium, Chroomonas, Cryptomonas, Hemiselmis, Chilomonas, Chlorella, Histiobranchus, Coryphaenoides, Thraustchytrium, Schizochytrium, Conidiobolus or Entomorphthora.

8. A production process of domestic fowl eggs having at least 3% arachidonic acid with respect to the total fatty acids contained in the egg yolk and optionally docosahexaenoic acid comprising feeding egg-layer domestic fowls with at least one ω6 highly unsaturated fatty acid selected from the group consisting of dihomo-γ-linolenic acid and arachidonic acid and optionally ω3 highly unsaturated fatty acid.

9. A process according to claim 8 wherein the ω6 highly unsaturated fatty acid is at least one fatty acid selected from the group consisting of, dihomo-γ-linolenic acid and arachidonic acid, that is used in at least one form selected from the group consisting of free fatty acid, salt, ester, triacylglycerol, diacylglycerol, monoacylglycerol, glycerophospholipid and sphingoglycolipid.

10. A process according to claim 8 wherein the ω6 highly unsaturated fatty acid is fed either alone or as a mixture in the form of (1) an oil or extract residue obtained by extracting from dried microbial cells or wet microbial cells of a microorganism having an ability to produce arachidonic acid or (2) dried or wet microbial cells of a microorganism having an ability to produce arachidonic acid.

11. A process according to claim 10 wherein said microorganism having the ability to produce arachidonic acid is of the genus Mortierella, Conidiobolus, Pythium, Phytophthora, Penicillium, Cladosporium, Mucor, Fusarium, Aspergillus, Rhodotorula, Entomophthora, Echinosporangium or Saprolegnia.

12. A process according to claim 8 wherein the ω3 highly unsaturated fatty acid is present and is at least one fatty acid selected from the group consisting of α-linolenic acid, 8,11,14,17-eicosatetraenoic acid, eicosapentaenoic acid, docosapentaenoic acid and docosahexaenoic acid, that is used in at least one form selected from the group consisting of free fatty acid, salt, ester, triacylglycerol, diacylglycerol, monoacylglycerol, glyerosphospholipid, glyceroglycolipid, sphingophospholipid and sphingoglycolipid.

13. A process according to claim 8 wherein the ω3 highly unsaturated fatty acid is fed either alone or as a mixture in the form of fish oil, fish powder, fish refuse, fish oil extract, an oil or extract residue obtained by extracting from dried or wet microbial cells of microorganism having the ability to produce docosahexaenoic acid, or dried or wet microbial cells of microorganism having the ability to produce docosahexaenoic acid.

14. A process according to claim 13 wherein the microorganism having the ability to produce docosahexaenoic acid is of the genus Crypthecodimium, Isochrysis, Nanochloropsis, Chaetoceros, Phaeodactylum, Amphidinium, Gonyaulax, Peridimium, Chroomonas, Cryptomonas, Hemiselmis, Chilomonas, Chlorella, Histiobranchus, Coryphaenoides, Thraustchytrium, Schizochytrium, Conidiobolus or Entomorphthora.

15. An egg yolk lipid having at least 3% arachidonic acid with respect to total fatty acids contained in the egg yolk lipid and optionally docosahexaenoic acid, wherein the egg yolk lipid is obtained from domestic fowl eggs obtained by feeding egg-laying domestic fowls with at least one ω6 highly unsaturated fatty acid selected from the group consisting of dihomo-γ-linolenic acid and arachidonic acid and optionally ω3 highly unsaturated fatty acid.

16. A lipid according to claim 15 wherein the ω6 highly unsaturated fatty acid is at least one fatty acid selected from the group consisting of, dihomo-γ-linolenic acid and arachidonic acid, that is used in at least one form selected from the group consisting of free fatty acid, salt, ester, triacylglycerol, diacylglycerol, monoacylglycerol, glycerophospholipid, glyceroglycolipid, sphingophospholipid and sphingoglycolipid.

17. A lipid according to claim 15 obtained from domestic fowl eggs obtained by feeding said ω6 highly unsaturated fatty acid either alone or as a mixture in the form of (1) an oil or extract residue obtained by extracting from dried microbial cells or wet microbial cells of a microorganism having an ability to produce arachidonic acid or (2) dried or wet microbial cells of a microorganism having an ability to produce arachidonic acid.

18. A lipid according to claim 17 wherein the microorganism having the ability to produce arachidonic acid is of the genus Mortierella, Conidiobolus, Pythium, Phytophthora, Penicillium, Cladosporium, Mucor, Fusarium, Aspergillus, Rhodotorula, Entomophthora, Echinosporangium or Saprolegnia.

19. A lipid according to claim 15 wherein the ω3 high unsaturated fatty acid is present and is at least one fatty acid selected from the group consisting of α-linolenic acid, 8,11,14,17-eicosatetraenoic acid, eicosapentaenoic acid, docosapentaenoic acid and docosahexaenoic acid, that is used in at least one form selected from the group consisting of free fatty acid, salt, ester, triacylglycerol, diacylglycerol, monocylglycerol, glyerophospholipid, glyceroglycolipid, sphingophospholipid and sphingoglycolipid.

20. A lipid according to claim 15 obtained from domestic fowl eggs obtained by feeding said ω3 highly unsaturated fatty acid either alone or as a mixture in the form of fish oil, fish powder, fish refuse, fish oil extract, an oil or extract residue obtained by extracting from dried or wet microbial cells of microorganism having the ability to produce docosahexaenoic acid, or dried or wet microbial cells of microorganism having the ability to produce docosahexaenoic acid.

21. A lipid according to claim 20 wherein the microorganism having the ability to produce docosahexaenoic acid is of the genus Crypthecodimium, Isochrysis, Nanochloropsis, Chaetoceros, Phaeodactylum, Amphidinium, Gonyaulax, Peridimium, Chroomonas, Cryptomonas, Hemiselmis, Chilomonas, Chlorella, Histiobranchus, Coryphaenoides, Thraustchytrium, Schizochytrium, Conidiobolus or Entomorphthora.

22. A lipid according to claim 15 that exhibits a ratio of 1 to 12 parts by weight of docosahexaenoic acid to 1 to 12 parts by weight of arachidonic acid, and exhibits a ratio of at least 5 parts by weight of arachidonic acid to 1 part by weight of eicosapentaenoic acid.

23. A process for producing an egg yolk lipid having at least 3% arachidonic acid with respect to total fatty acids contained in the egg yolk lipid and optionally docosahexaenoic acid, said process comprising extracting said egg yolk lipid from domestic fowl eggs obtained by feeding egg laying domestic fowls with at least one ω6 highly unsaturated fatty acid selected from the group consisting of dihomo-γ-linolenic acid and arachidonic acid and optionally ω3 highly unsaturated fatty acid.

24. A process according to claim 23 wherein the ω6 highly unsaturated fatty acid is at least one fatty acid selected from the group consisting of, dihomo-γ-linolenic acid and arachidonic acid, that is used in at least one form selected from the group consisting of free fatty acid, salt, ester, triacylglycerol, diacylglycerol, monoacylglycerol, glycerophospholipid, glyceroglycolipid, sphingophospholipid and sphingoglycolipid.

25. A process according to claim 23 wherein the lipid is extracted from domestic fowl eggs obtained by feeding said ω6 highly unsaturated fatty acid either alone or as a mixture in the form of (1) an oil or extract residue obtained by extracting from dried microbial cells or wet microbial cells of a microorganism having an ability to produce arachidonic acid or (2) dried or wet microbial cells of a microorganism having an ability to produce arachidonic acid.

26. A process according to claim 25 wherein the microorganism having the ability to produce arachidonic acid is of the genus Mortierella, Conidiobolus, Pythium, Phytophthora, Penicillium, Cladosporium, Mucor, Fusarium, Aspergillus, Rhodotorula, Entomophthora, Echinosporangium or Saprolegnia.

27. A process according to claim 23 wherein the ω3 highly unsaturated fatty acid is present and is at least one fatty acid selected from the group consisting of α-linolenic acid, 8,11,14,17-eicosatetraenoic acid, eicosapentaenoic acid, docosapentaenoic acid and docosahexaenoic acid, that is used in at least one form selected from the group consisting of free fatty acid, salt, ester, triacylglycerol, diacylglycerol, monoacylglycerol, glyerophospholipid, glyceroglycolipid, sphingophopholipid and sphingoglycolipid.

28. A process according to claim 23 wherein the lipid is extracted from domestic fowl eggs obtained by feeding said ω3 highly unsaturated fatty acid either alone or as a mixture in the form of fish oil, fish powder, fish refuse, fish oil extract, an oil or extract residue obtained by extracting from dried or wet microbial cells of microorganism having the ability to produce docosahexaenoic acid, or dried or wet microbial cells of microorganism having the ability to produce docosahexaenoic acid.

29. A process according to claim 28 wherein the microorganisms having the ability to produce docosahexaenoic acid is of the genus Crypthecodimium, Isochrysis, Nanochlorolsis, Chaetoceros, Phaeodactylum, Amphidinium, Gonyaulax, Peridimium, Chroomonas, Cryptomonas, Hemiselmis, Chilomonas, Chlorella, Histiobranchus, Coryphaenoides, Thraustchytrium, Schizochytrium, Conidiobolus or Entomorphthora.

30. A process according to claim 23 comprising extracting a lipid exhibiting a ratio of 1 to 12 parts by weight of docosahexaenoic acid to 1 to 12 parts by weight of arachidonic acid, and exhibiting a ratio of at least 5 parts by weight of arachidonic acid to 1 part by weight of eicosapentaenoic acid.

31. A food having arachidonic acid and optionally docosahexaenoic acid comprising at least 0.001% by weight of an egg yolk lipid having at least 3% arachidonic acid with respect to the total fatty acids contained in the egg yolk lipid and optionally docosahexaenoic acid, wherein said food is obtained by adding to a food an egg yolk lipid, wherein said egg yolk lipid is extracted from domestic fowl eggs obtained by feeding egg-laying domestic fowls with at least one ω6 highly unsaturated fatty acid selected from the group consisting of dihomo-γ-linolenic acid and arachidonic acid and optionally ω3 highly unsaturated fatty acid.

32. A food according to claim 31 wherein the ω6 highly unsaturated fatty acid is at least one fatty acid selected from the group consisting of, dihomo-γ-linolenic acid and arachidonic acid, that is used in at least one form selected from the group consisting of free fatty acid, salt, ester, triacylglycerol, diacylglycerol, monoacylglycerol, glycerophospholipid, glyceroglycolipid, sphingophospholipid and sphingoglycolipid.

33. A food according to claim 31 obtained by adding a lipid having at least 3% arachidonic acid with respect to total fatty acids contained in the lipid, wherein the lipid is obtained from domestic fowl eggs obtained by feeding said ω6 highly unsaturated fatty acid either alone or as a mixture in the form of (1) an oil or extract residue obtained by extracting from dried microbial cells or wet microbial cells of microorganism having an ability to produce arachidonic acid or (2) dried or wet microbial cells of microorganism having an ability to produce arachidonic acid.

34. A food according to claim 33 wherein the microorganisms having the ability to produce arachidonic acid is of the genus Mortierella, Conidiobolus, Pythium, Phytophthora, Penicillium, Cladosporium, Mucor, Fusarium, Aspergillus, Rhodotorula, Entomophthora, Echinosporangium or Saprolegnia.

35. A food according to claim 31 wherein the ω3 highly unsaturated fatty acid is present and is at least one of the fatty acids selected from the group consisting of α-linolenic acid, 8,11,14,17-eicosatetraenoic acid, eicosapentaenoic acid, docosapentaenoic acid and docosahexaenoic acid, that is used in at least one form selected from the group consisting of free fatty acid, salt, ester, triacylglycerol diacylglycerol, monocylglycerol, glyerophospholipid, glyceroglycolipid, sphingophospholipid and sphingoglycolipid.

36. A food according to claim 31 obtained by adding a lipid having a ratio of 1 to 12 parts by weight of docosaphexaenoic acid to 1 to 12 parts by weight of arachidonic acid obtained from domestic fowl eggs obtained by feeding said ω3 highly unsaturated fatty acid either alone or as a mixture in the form of fish oil, fish powder, fish refuse, fish oil extract, an oil or extract residue obtained by extracting from dried or wet microbial cells of microorganism having the ability to produce docosaphexaenoic acid, or dried or wet microbial cells of microorganism having the ability to produce docosahexaenoic acid.

37. A food according to claim 36 wherein said microorganism having the ability to produce docosahexaenoic acid is of the genus Crypthecodimium, Isochrysis, Nanochloropsis, Chaetoceros, Phaeodactylum, Amphidinium, Gonyaulax, Peridimium, Chroomonas, Cryptomonas, Hemiselmis, Chilomonas, Chlorella, Histiobranchus, Coryphaenoides, Thraustchytrium, Schizochytrium, Conidiobolus or Entomorphthora.

38. A food according to claim 31 wherein said food is a formula suitable for feeding premature infants, formula suitable for feeding infants, a follow-up formula or as a milk product for expectant or nursing mothers.

* * * * *

UNITED STATES PATENT AND TRADEMARK OFFICE
CERTIFICATE OF CORRECTION

PATENT NO.     : 6,432,468 B1                                                Page 1 of 1
DATED          : August 13, 2002
INVENTOR(S)    : Kengo Akimoto et al.

It is certified that error appears in the above-identified patent and that said Letters Patent is hereby corrected as shown below:

<u>Title page,</u>
Please correct the Assignee's Information from
"[73]   Assignee: Suntory Limited, Osaka (JP)" to
-- [73]   Assignees: Suntory Limited, Osaka (JP), Bizen Chemical Co., Ltd., Okayama (JP) and NOF Corporation, Tokyo (JP) --

Signed and Sealed this

First Day of July, 2003

JAMES E. ROGAN
*Director of the United States Patent and Trademark Office*